United States Patent [19]
Jakob et al.

[11] Patent Number: 5,659,140
[45] Date of Patent: Aug. 19, 1997

[54] TESTING MACHINE FOR PAVEMENT SAMPLES

[75] Inventors: Herbert E. Jakob, Chattanooga, Tenn.; M. Earl Edwards, Jr., Trenton, Ga.

[73] Assignee: Pavement Technology, Inc., Chattanooga, Tenn.

[21] Appl. No.: 689,602

[22] Filed: Aug. 13, 1996

[51] Int. Cl.$^6$ .................... G01N 3/00; G01N 11/00
[52] U.S. Cl. ........................................ 73/788; 73/790
[58] Field of Search ..................... 73/146, 788, 790, 73/794, 795, 796, 797

[56] References Cited

U.S. PATENT DOCUMENTS

| | | | |
|---|---|---|---|
| 4,942,768 | 7/1990 | McRae | 73/795 |
| 4,958,306 | 9/1990 | Powell et al. | 73/146 |
| 5,248,200 | 9/1993 | Walsh | 73/787 |

OTHER PUBLICATIONS

"Development and Use of Georgia Loaded Wheel Tester" by Ronald Collins, Donald Watson, and Bruce Campbell (no date).

"Development of a Simplified Test Method to Predict Rutting Characteristics of Asphalt Mixes" by James S. Lai (Georgia Institute of Technology); Prepared for Department of Transportation State of Georgia; Jul., 1986.

"Evaluation of Rutting Characteristics of Asphalt Mixes Using Loaded–Wheel Tester" by James S. Lai (Georgia Institute of Technology); Prepared for Georgia Department of Transportation Office of Materials and Research; Dec., 1986.

"Evaluation of The Effect of Gradation of Aggregate on Rutting Characteristics of Asphalt Mixes" by James S. Lai (Georgia Institute of Technology); Prepared for Georgia Department of Transportation Office of Materials & Research; Aug., 1988.

"Development of A Laboratory Rutting Resistance Testing Method for Asphalt Mixes" by James S. Lai (Georgia Institute of Technology); Prepared for Georgia Department of Transportation Office of Materials and Research; Aug., 1989.

*Primary Examiner*—George M. Dombroske
*Assistant Examiner*—Max H. Noori
*Attorney, Agent, or Firm*—Chambliss, Bahner & Stophel, P.C.

[57] ABSTRACT

An apparatus for testing pavement test samples for for surface wear, including rutting, stripping and fatigue, is disclosed. The testing machine includes a testing chamber and a sample tray that is adapted for holding one or more test samples. The machine also includes a hose for each test sample to be tested. Each hose is disposed above a test sample in the sample tray in such fashion that the hose may be deflected to contact a least a substantial portion of the sample. A mechanism is also provided for pumping a fluid into each hose and for maintaining fluid pressure within the hose. The testing machine also includes a testing wheel assembly that is disposed above the hose assembly within the chamber. The testing wheel assembly is adapted for reciprocating movement on a track and includes a loading wheel for each hose. A loading cylinder is also provided for each loading wheel, with cylinder is adapted for applying a downwardly directed load to such wheel as the loading wheel moves back and forth along a hose that is in contact with sample beneath. The testing machine also includes an immersion pan into which a sample tray may be placed in the chamber, and a mechnism is provided for filling the immersion pan with water. Also provided is a temperature controlling mechanism for controlling temperature in the testing chamber.

10 Claims, 10 Drawing Sheets

TESTING MACHINE FOR PAVEMENT SAMPLES

FIELD OF THE INVENTION

The invention relates to testing apparatus and methods, and more particularly to a testing machine for use in testing samples of asphalt pavement compositions or asphalt concrete compositions for surface wear, including rutting and stripping, and fatigue. The machine may therefore be used to perform tests on samples of asphalt pavement compositions that will permit a prediction of the durability, serviceability and overall suitability of such compositions for use in roadway construction.

BACKGROUND OF THE INVENTION

The durability and service performance of an asphalt roadway can be affected by a number of variables, including the asphalt mix composition that is used, the construction techniques employed in building the roadway, the overall weight and the axle weight of the vehicles using the roadway, the number and speed of the vehicles and the temperature and other environmental factors under which the roadway is used. Most of these various factors are beyond the control of the road designer. Furthermore, as traffic has increased on the nation's highways and as high-pressure radial tires have become more commonly used on heavy trucks, wear and even deterioration of the roadways has accelerated. Therefore, construction techniques and especially the design and selection of asphalt paving mix compositions have assumed much greater significance than was previously the case. In particular, the design and selection of asphalt paving mix compositions have become more critical in building roads than ever before.

This increased importance in the design and selection of asphalt paving compositions has led to greater emphasis in recent years in developing testing apparatus and methods that can be useful in predicting the performance characteristics of asphalt paving compositions. The ability to predict such performance characteristics as rutting, stripping and fatigue cracking from a sample of a particular asphalt paving composition can lead to the development of improved and longer-lasting paving compositions.

Generally, pavement rutting will be due to inadequacy of the pavement system under the prevailing traffic and environmental conditions. Rutting is a manifestation of differential surface deformation in the wheel paths of a roadway which results from selective densification and shear deformation. Generally, the amount of pavement rutting depends, at least in part, on the traffic loads placed on the roadway and the distribution of such loads across the roadway. It will also be affected by the stresses introduced into the pavement system, and by the permanent strains induced as a result of these stresses. These permanent strains will depend on the permanent deformation characteristics of the layer materials, particularly the asphalt concrete layer.

Rutting reduces road serviceability and driving comfort and will reduce the service life of a roadway. In addition, rutting may also contribute to safety hazards that may arise from an accumulation of water in the rutting paths. Such accumulation may lead to hydroplaning, or in appropriate weather conditions, icing.

Because a tendency towards rutting can depend to a significant degree on the composition of the asphalt mix that is used, methods and apparatus for use in predicting rutting tendencies in various asphalt compositions have assumed increasing importance and emphasis. Beginning in 1985, the Georgia Department of Transportation and the Georgia Institute of Technology, in cooperation with the Federal Highway Administration and the U.S. Department of Transportation, embarked on a program to develop a testing machine that could accurately predict the rutting characteristics of highway paving compositions. This program resulted in the development of the Georgia Loaded Wheel Tester, an apparatus designed to test samples of asphalt compositions for rutting characteristics, and in the establishment of the GDT-115 testing procedure for rutting susceptibility. The study began with evaluation of a loaded wheel tester that had been used by the Georgia Department of Transportation Materials Testing Laboratory for design and testing of slurry seals. This machine was developed by Benedict Slurry Seal, Inc. of Dayton Ohio. It consists essentially of a one inch (2.54 cm) wide by three inch (7.62 cm) diameter hard rubber caster-type wheel mounted on a frame. A box to hold lead shot was mounted atop the wheel for providing a load. This loaded wheel was driven across a pavement sample through a twelve inch (30.48 cm) reciprocating stroke by a 0.25 hp (186.5 watt), 1750 rpm motor operated through a gear reducer at a ratio of 40:1 to provide 44 cycles per minute, where one cycle comprises two passes over the sample. The machine was operated in an airtight temperature-controlled room that was heated to simulate the effects of hot weather on rutting. The use of this apparatus did not provide satisfactory results, principally because it could not simulate the effect of high-pressure tires on the roadway. Subsequently, the Benedict apparatus was modified to include consideration of tire pressure on rutting. This modified machine, known as the Georgia Loaded Wheel Tester, employed an eight inch (20.32 cm) diameter aluminum wheel with a one inch (2.54 cm) diameter high-pressure rubber hose wrapped around it in the shape of a tire. The hose selected was capable of being pressurized at a pressure of up to 120 psi (828 kPa). This version of the apparatus was also found to be unsatisfactory, primarily because of excessive wear of the "hose-tire" due to skidding at the ends of the reciprocating stroke. This skidding also caused excessive rutting in the asphalt concrete samples at these locations.

The Georgia Loaded Wheel Tester was then modified to eliminate the "hose-tire" in favor of a high-pressure linearly disposed hose, which was placed on top of the asphalt concrete specimen and pressurized to simulate tire pressure. The hose was held in position on both ends by end clamps. A three inch (7.62 cm) diameter aluminum wheel with a concave rim was then attached to the reciprocating arm so as to ride atop the linear hose. As the machine was operated, the wheel riding along the hose was judged capable of simulating pressurized tire contact with the sample. The power rating of the motor for providing reciprocating motion was also increased to one-third horsepower (248.7 watts). The entire machine was also enclosed in an environmental chamber (instead of an environmentally-controlled room) which was capable of maintaining a constant temperature of up to 120° F. throughout the test period. Enclosing only the test portion of the machine in an environmental chamber was considered but not deemed to provide sufficient temperature control as was required for test repeatability. This version of the Georgia Loaded Wheel Tester was also equipped with a preheating box to precondition pavement samples to the testing temperature prior to testing. In addition, a channel section having seven slots at two-inch (5.08 cm) intervals was developed to be placed over the sample for measuring the rut profile developed as a result of the testing. A dial gauge was used to measure the rutting developed at each of the seven locations in the sample defined by the slots in the channel section.

Finally, the machine was modified yet again. In the latest version of the Georgia Loaded Wheel Tester, the sample holder has been modified to accommodate three samples, and three loaded wheels are provided for simultaneous testing of the samples. Furthermore, in order to accommodate this expansion of the capacity of the machine, the portion of the apparatus undergoing reciprocating motion was changed from the loaded wheel or wheels to the sample or samples. The loaded wheels are held stationary, and the samples, each with its associated linearly disposed high-pressure hose, are moved back and forth therebeneath.

The Georgia Loaded Wheel Tester represents a significant advance in the technology of predicting rutting in pavement samples. However, it suffers from several shortcomings. Because it must be totally enclosed in an environmental chamber, it is not sufficiently portable to be readily capable of use in field laboratories. In addition, enclosing the entire machine in a chamber that is heated to simulate the effects of hot summertime weather puts the reciprocating motor and other components of the machine at risk of overheating. The Georgia Loaded Wheel Tester is also subject to excessive vibration during operation. The sample holder or carriage with its three samples is quite massive, and considerable vibration is developed by its reciprocating motion. Finally, although rutting is an important component of pavement failure, it is not the only such component. Prediction of susceptibility of pavement designs to other types of failure could also be quite valuable.

It would be advantageous, therefore, if a testing machine could be developed that is more portable and more versatile than the Georgia Loaded Wheel Tester, and that avoids its disadvantages and inadequacies.

OBJECTS AND ADVANTAGES OF THE INVENTION

Accordingly, it is an object of the invention claimed herein to provide a testing machine for use in testing samples of asphalt pavement compositions to predict the ruffing tendencies of such compositions, which machine is sufficiently portable to be used in field test laboratories. It is another object of the invention to provide such a testing machine that employs a reciprocating mechanism that does not have to be totally enclosed in a heated chamber for use. It is yet another object of the invention to provide such a testing machine that employs a reciprocating mechanism that is lighter in weight and more efficient than that of previously known machines. Another object of the invention is to provide a testing machine that may be used in testing samples of asphalt pavement compositions for fatigue and surface wear, including rutting and stripping in order to permit prediction of the durability, serviceability and overall suitability of such compositions for use in roadway construction.

Additional objects and advantages of this invention will become apparent from an examination of the drawings and the ensuing description.

EXPLANATION OF TECHNICAL TERMS

As used herein, "fatigue" refers to the tendency of an asphalt concrete pavement system to develop cracks under loads applied by vehicles. Premature fatigue cracking generally occurs when asphalt concrete is improperly supported by underlying components of the paving system or when the asphalt concrete composition is improperly designed.

As used herein, "rutting" refers to the tendency of an asphalt concrete pavement to be differentially deformed or compacted in the wheel paths of vehicular traffic. Rutting is a manifestation of densification and shear deformation and is caused by stresses induced in the pavement system and the permanent strains induced as a result of the stresses developed.

As used herein, "stripping" refers to the tendency of the asphalt cement component of an asphalt concrete pavement composition to be stripped out or washed away by water as the pavement is subjected to traffic. Stripping may occur when traffic loads are applied to pavement during rainfall, snowfall or the like, and its effect may be to erode the pavement as the asphalt cement component is stripped away from the aggregate particles which it binds together.

SUMMARY OF THE INVENTION

The invention comprises an apparatus for testing one or more pavement test samples. The apparatus includes a frame which supports and encloses a testing chamber, and a sample tray that is supported by the frame within the chamber and is adapted for holding one or more test samples. A hose assembly is also included, which assembly is supported by the frame and disposed above the sample tray within the chamber. The hose assembly includes one or more elongated, hollow, flexible hoses, and a hose is provided for each sample to be tested. The hose assembly also includes a hose rack which is adapted for supporting a pair of hose shanks for each hose, one at each side of the rack, so that each hose may be attached at each end to a hose shank and thereby disposed, along an axis extending generally in a straight line from one side of the rack to the opposite side, above a test sample in the sample tray in such fashion that the hose may be deflected to contact at least a substantial portion of the sample. The hose assembly also includes means for pumping a fluid into each hose and for maintaining fluid pressure within the hose so as to apply a resulting pressure to the interior walls of the hose. The apparatus also includes a testing wheel assembly that is supported by the frame and disposed above the hose assembly within the chamber. This testing wheel assembly includes a loading wheel carrier which is adapted for reciprocating movement on a track, and an elongated loading wheel arm for each hose, which arm has a first end and a second end, wherein said first end is pivotally attached to the loading wheel carrier. The testing wheel assembly also includes a loading wheel for each arm, which wheel is mounted on an axis that is supported at the second end of the arm, so that each wheel is disposed above a hose. The testing wheel assembly also includes a loading cylinder for each loading wheel, which cylinder is mounted on the loading wheel carrier and adapted for applying a downwardly-directed load to such wheel, whereby such wheel will contact a hose and deflect the hose downwardly onto a sample. The testing wheel assembly also includes means for imparting reciprocating movement to the loading wheel carrier along the track at a controlled rate, so that each wheel will move back and forth along a hose. The apparatus also includes an immersion pan into which the sample tray may be placed in the chamber without mechanical interference between the pan and the hose assembly or between the pan and the testing wheel assembly, means for filling the immersion pan with water, and means for controlling the temperature in the testing chamber. In the operation of the apparatus, one or more test samples may be placed in the sample tray, and a fluid may be pumped into each hose and fluid pressure maintained therein so as to apply a resulting pressure to the interior walls of each hose.

In order to test one or more pavement samples for fatigue, the loading cylinder for each loading wheel is actuated so as to apply a downwardly-directed load to each such wheel, so that each wheel will contact a hose under the influence of the load and deflect such hose downwardly onto a sample, so as to simulate a force that is applied to the pavement by a wheel of a vehicle. Reciprocating movement is then imparted to the loading wheel carrier along the track at a controlled rate, while the loading cylinder for each loading wheel applies a downwardly-directed load to each such wheel, so that each wheel will move back and forth along a hose while under the influence of the load. The effect of such reciprocating movement under load on the sample can then be gauged to determine the effect of fatigue on the sample.

In order to test for rutting of the samples, reciprocating movement is imparted to the loading wheel carrier along the track at a controlled rate, while the loading cylinder for each loading wheel is actuated so as to apply a downwardly-directed load to each such wheel. Each wheel will contact a hose under the influence of the load and deflect such hose downwardly onto a sample, as the wheel moves back and forth along the hose while under the influence of the load. The effect of such reciprocating movement under load can then be gauged to determine the rutting tendency of the samples.

In order to test for stripping, the samples are placed into the immersion pan in the chamber, and the pan is filled with water. Reciprocating movement is then imparted to the loading wheel carrier along the track while the loading cylinder for each loading wheel is actuated so as to apply a downwardly-directed load to each such wheel. Each wheel will contact a hose under the influence of the load and deflect such hose downwardly onto a sample, as the wheel moves back and forth along the hose while under the influence of the load, and the effect of such reciprocating movement under load on the submerged samples can then be gauged to determine the stripping tendency of the samples.

In order to facilitate an understanding of the invention, the preferred embodiment of the invention is illustrated in the drawings, and a detailed description thereof follows. It is not intended, however, that the invention be limited to the particular embodiment described or to the particular apparatus illustrated herein. Various changes are contemplated such as would ordinarily occur to one skilled in the art to which the invention relates.

DESCRIPTION OF THE PREFERRED EMBODIMENTS

Figure 1:
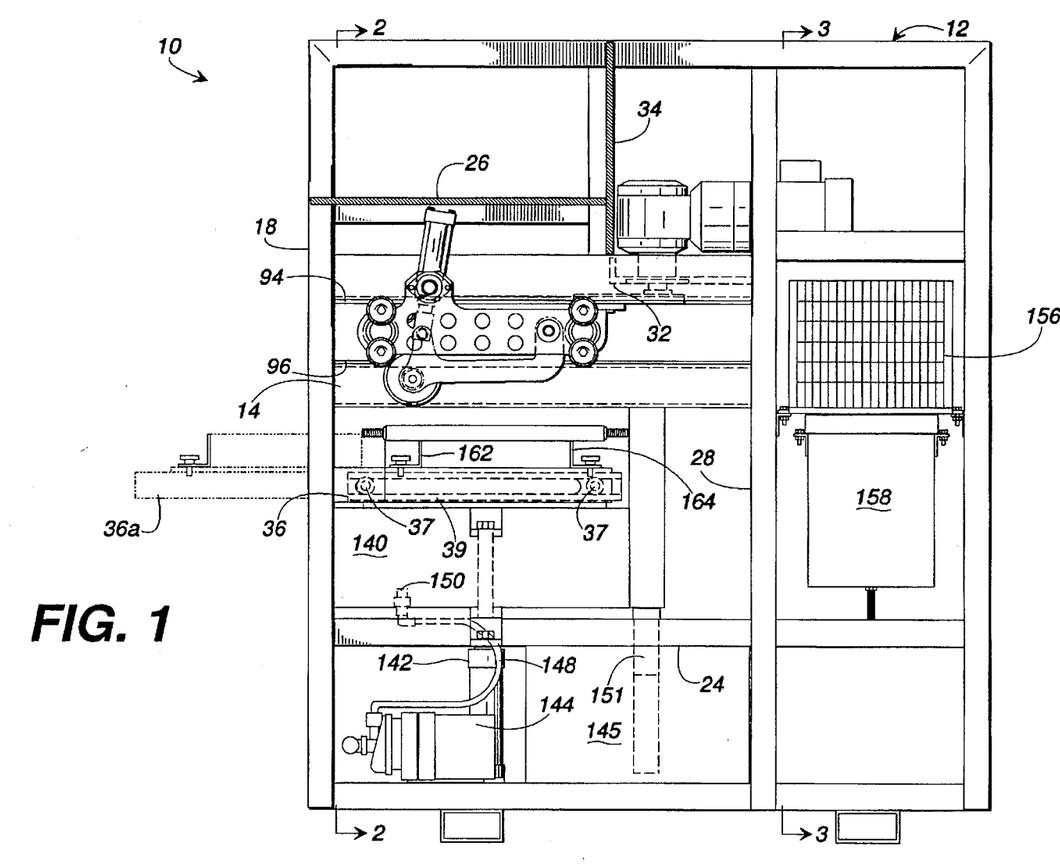
FIG. 1 is a plan view of a preferred embodiment of the invention.
Figure 2:
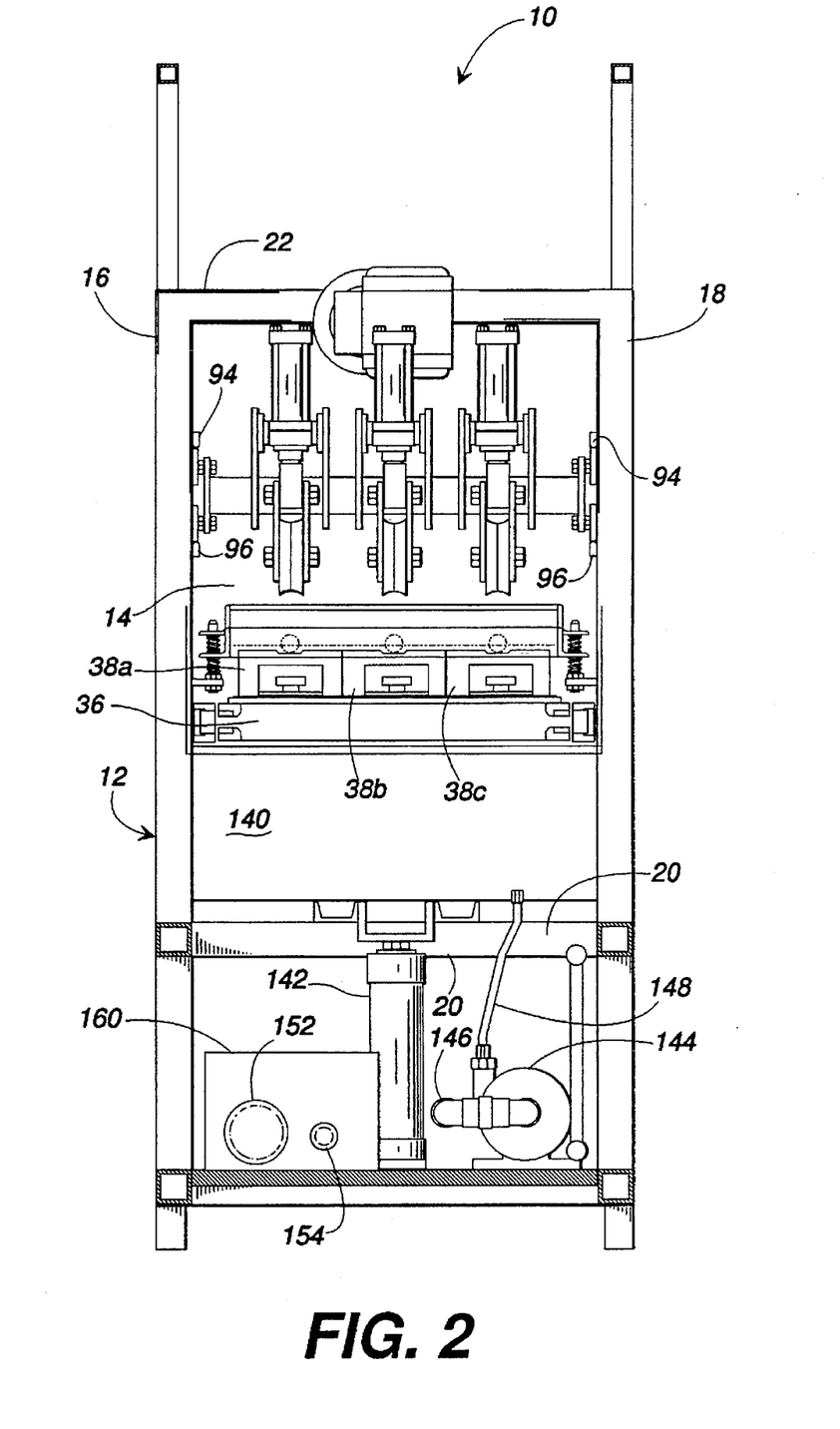
FIG. 2 is a sectional view of a portion of the apparatus of FIG. 1, taken along the line 2—2 of FIG. 1.
Figure 3:
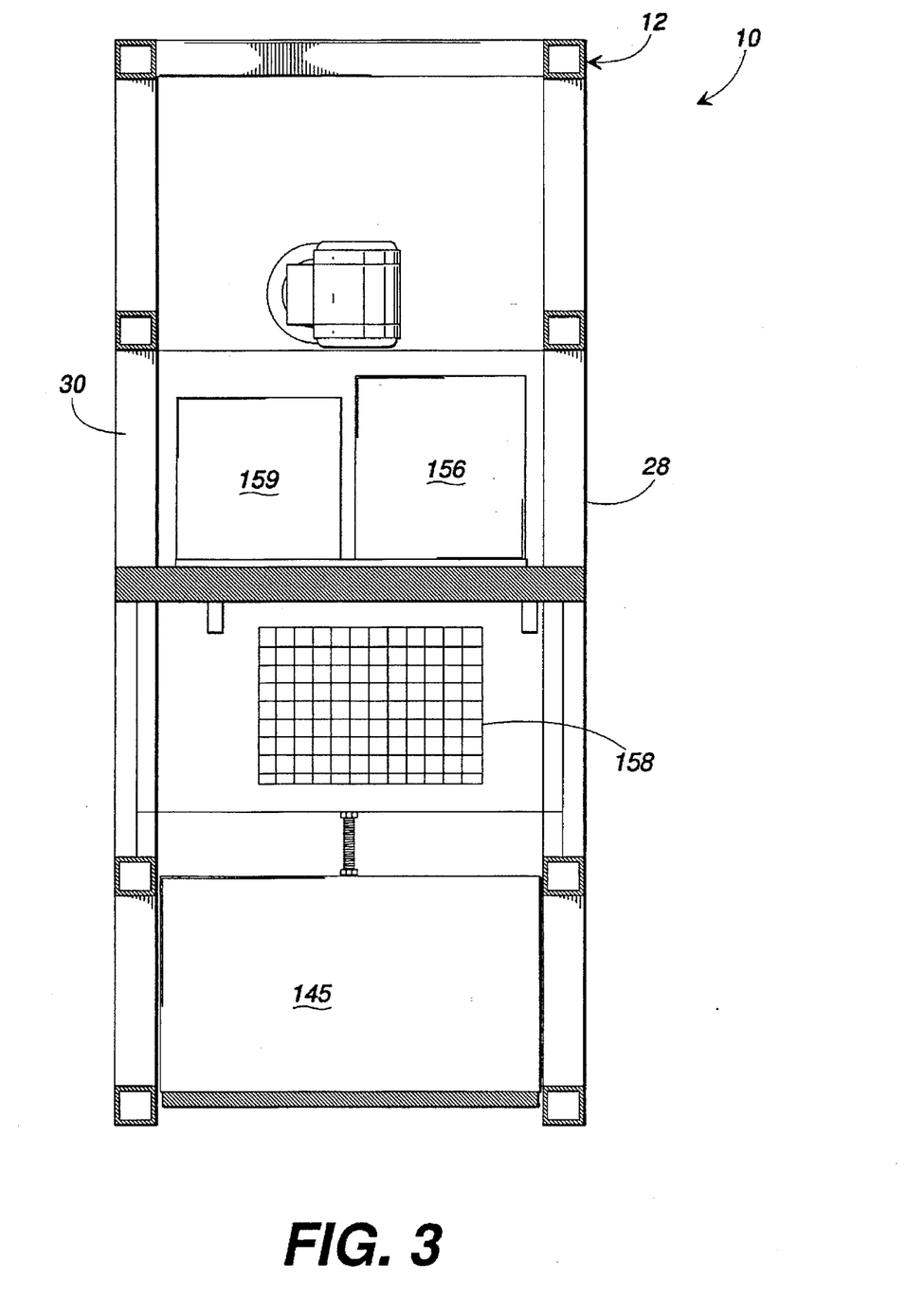
FIG. 3 is a sectional view of a portion of the apparatus of FIG. 1, taken along the line 3—3 of FIG. 1.

FIGS. 1 through 3 illustrate a preferred embodiment of the invention, which is an apparatus for testing samples of asphalt pavement compositions or asphalt concrete compositions for surface wear, including rutting and stripping, and fatigue, in order to permit prediction of the durability, serviceability and overall suitability of such compositions for use in roadway construction. Referring now to the drawings, apparatus 10 includes a frame 12 comprised primarily of a plurality of steel channel pieces welded or otherwise joined together, in the configuration illustrated, in a known fashion. Of course, the frame could be provided in any convenient configuration, so long as it is adapted to support the other components of the apparatus and to enclose a testing chamber. As shown in FIGS. 1 through 3, frame 12 encloses testing chamber 14 within the space defined by frame components 16, 18, 20, 22, 24, 26, 28, 30, 32 and 34.

Supported by the frame within the testing chamber is sample tray 36 that is adapted for holding one or more test samples, such as samples 38a, 38b and 38c (best shown in FIG. 2). Preferably, the sample tray is mounted by means of wheels 37 on track 39, in rolling engagement therewith, or it may otherwise be adapted to slide or roll out of the chamber in the manner of a drawer or by other convenient means, to provide convenient access to the samples in the tray. The tray may be slid from a first position beneath the hose assembly and the testing wheel assembly to a second position that provides more convenient access to the samples in the tray, and such second position is shown in phantom lines at 36a in FIG. 1.

Figure 4:
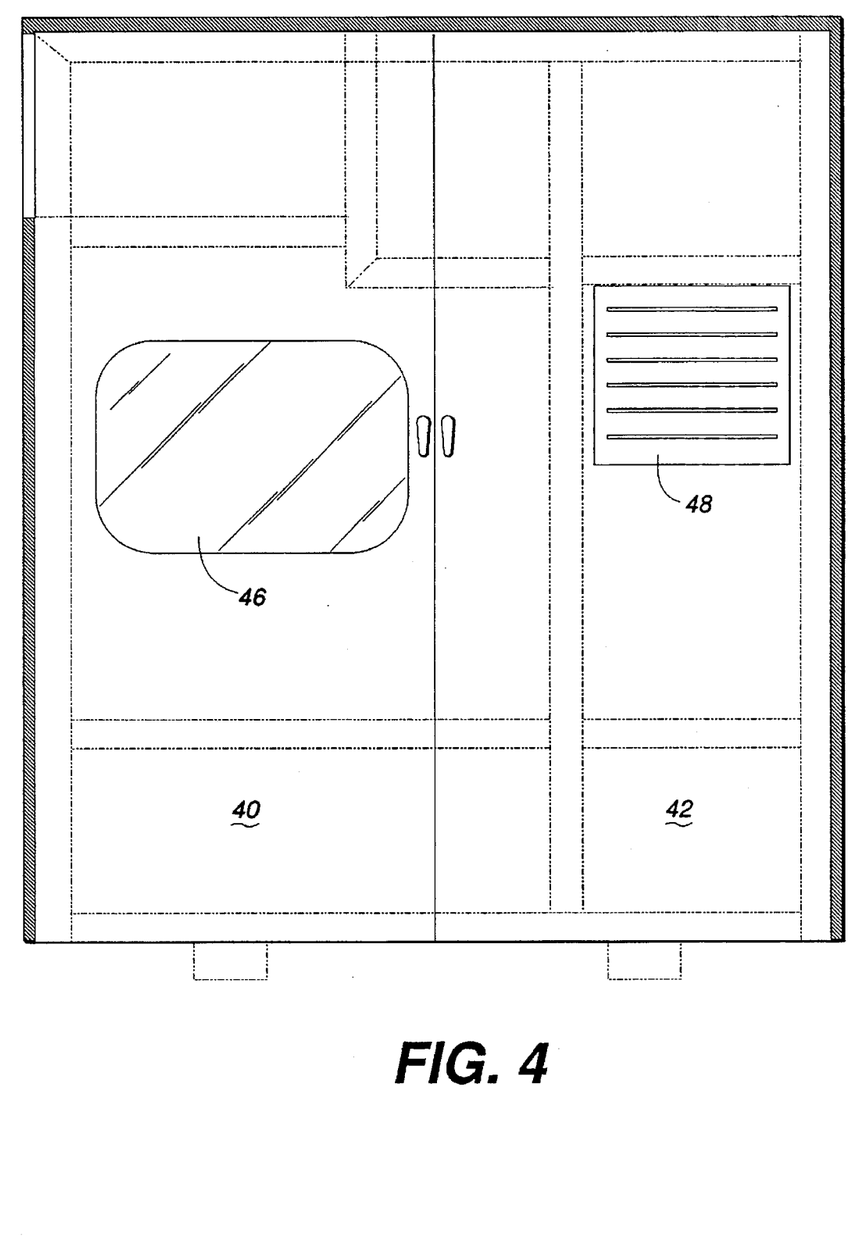
FIG. 4 is a plan view of the cabinet enclosure of the apparatus of FIG. 1.
Figure 5:
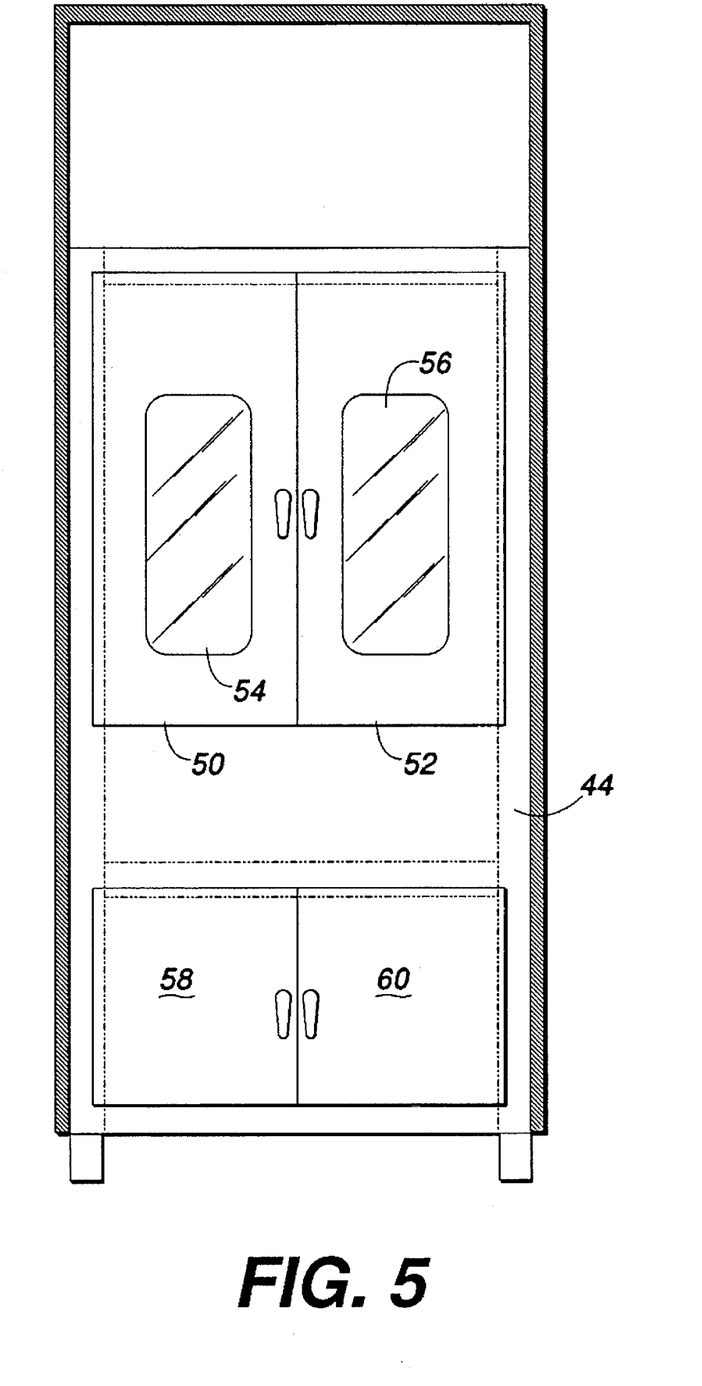
FIG. 5 is a view of the left side of the cabinet enclosure of FIG. 4, as viewed from the perspective of FIG. 4.

FIGS. 4 and 5 illustrate a preferred cabinet enclosure for the apparatus shown in FIGS. 1 through 3, which includes front doors 40 and 42, left side panel 44, and right side and rear panels (not shown). As shown in FIG. 4, door 40 includes window 46, which permits viewing of a portion of the testing chamber 14. In addition, door 42 includes louver 48, the purpose of which will be subsequently explained. As shown in FIG. 5, left side panel 44 includes upper access doors 50 and 52, which include windows 54 and 56 respectively. These windows also permit viewing of a portion of testing chamber 14. In addition, a comparison of FIGS. 2 and 5 will reveal that opening of doors 50 and 52 will permit access to the sample tray (and the samples contained therein), and will permit the tray to be rolled out of the chamber to facilitate such access. In addition, lower doors 58 and 60 in panel 44 provide access to certain components of the testing machine outside of the testing chamber, as will be subsequently explained.

Figure 1A:
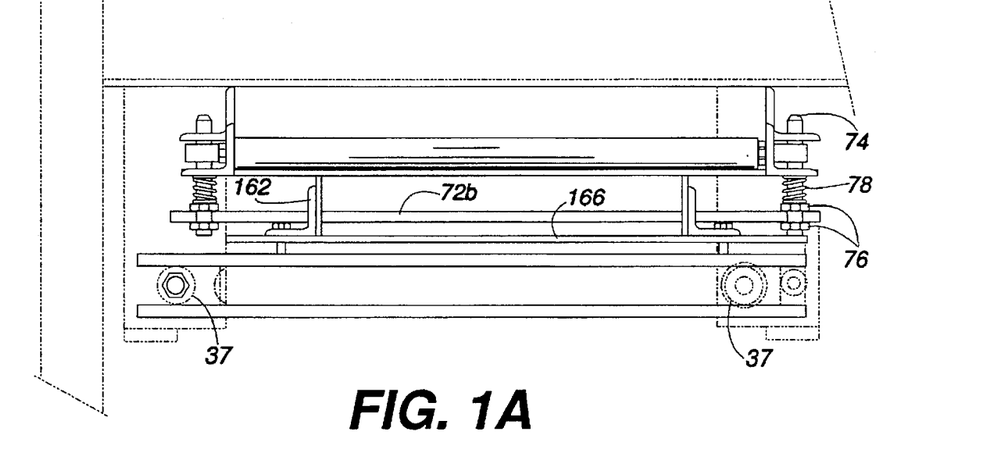
FIG. 1A is an enlarged view of a portion of FIG. 1.
Figure 2A:
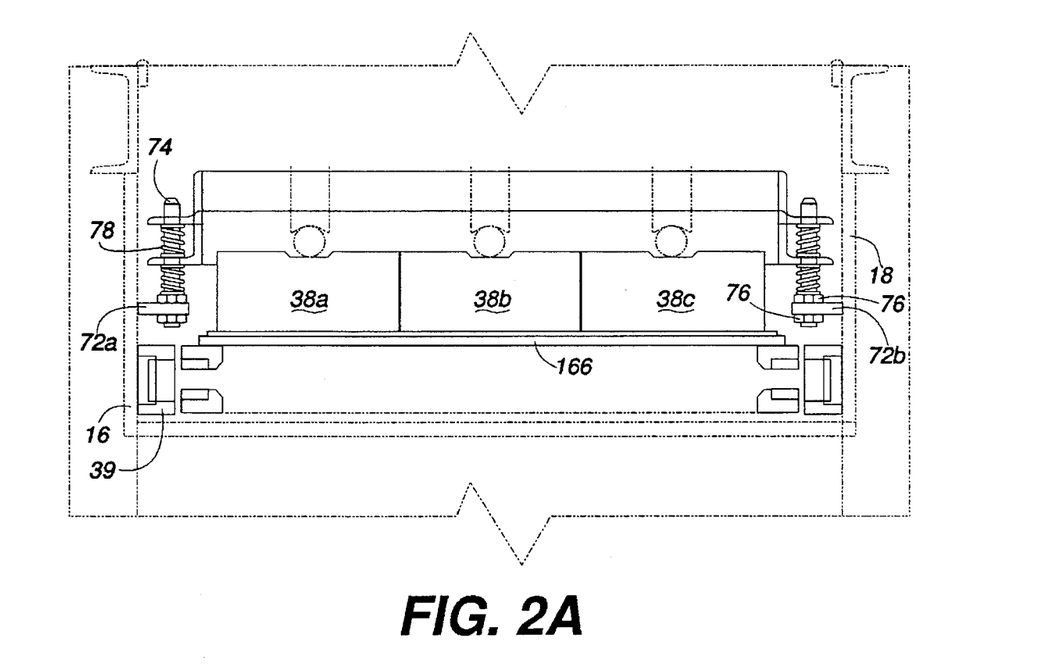
FIG. 2A is an enlarged view of a portion of FIG. 2.
Figure 6:
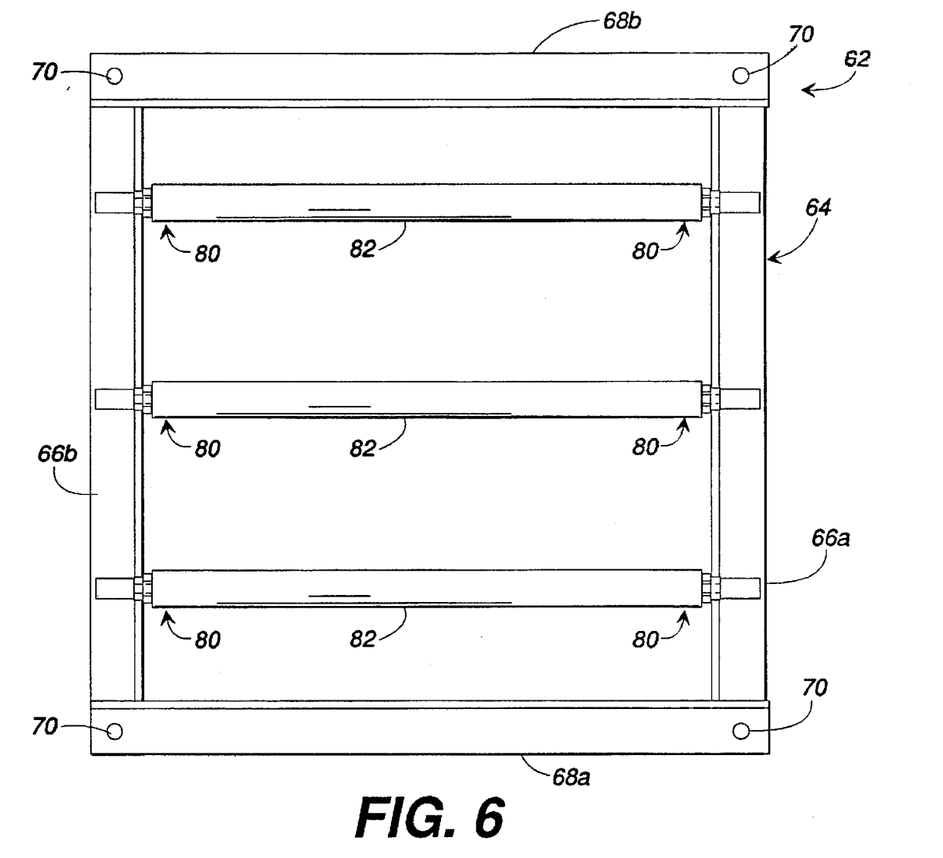
FIG. 6 is a top view of a portion of the hose rack assembly of the apparatus of FIG. 1.

Within the testing chamber, as best shown in FIGS. 1A, 2A and 6, is provided a hose assembly 62, which is supported by the frame 12 and disposed above sample tray 36 within chamber 14. As shown in FIG. 6, hose rack 64 is comprised of two angled side pieces 66a and 66b, and two angled end pieces 68a and 68b, preferably made of stainless steel. The four components of hose rack 64 are welded or otherwise joined together by any convenient means. Each of end pieces 68a and 68b are provided with a pair of holes 70, one at each end, which are used to mount the hose rack to the frame. A pair of hose rack support members 72a and 72b are attached to frame components at either side of the testing chamber (as shown in FIG. 2A), including components 16 and 18, by welding or other convenient means. The support members are preferably provided with four holes which may be aligned with holes 70 in the end pieces. A bolt 74 is placed into each of the holes in the support members and secured thereto by means of a pair of jam nuts 76. A compression spring such as spring 78 is then preferably placed over each bolt, and the hose rack placed thereover so that bolts 74 protrude through holes 70. Springs 78 will urge the hose rack upwardly so that it will be supported above sample tray 36. Of course, the hose rack may be supported by the frame of the apparatus within the testing chamber by other convenient and useful means as are known.

Figure 6A:
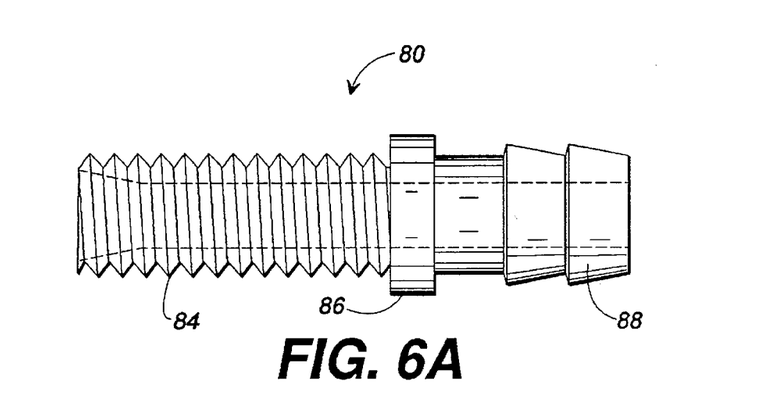
FIG. 6A is an enlarged view of a portion of FIG. 6.

Side pieces 66a and 66b are each provided with a plurality of holes, preferably three (as illustrated in FIG. 6), each of which is adapted for receiving a hose shank 80 (best shown in FIG. 6A). A pair of hose shanks is provided for mounting each elongated, hollow, flexible hose 82, one of which is provided for each test sample to be tested. The hose shank is a hollow, tube-like member that has a threaded portion 84 on one end, an intermediate stop portion 86, and a hose coupling portion 88 at the end opposite the threaded portion. The threaded portion 84 of each hose shank is adapted to be placed in each of the holes in side pieces 66a and 66b from the inside of the hose rack so that the stop portion 86 will bear against the inside surface of a side piece with the hose coupling portion 88 disposed towards the inside of the hose rack. As shown in FIG. 6, hose shanks 80 are disposed oppositely from each other across the hose rack, so that a hose 82 may be attached at each end to a hose shank and thereby disposed, along an axis extending generally in a straight line from one side of the rack to the opposite side, above a test sample in the sample tray in such fashion that the hose may be deflected to contact at least a substantial portion of the sample. Hose shanks 80 may be secured to the hose rack by threading jam nuts (not shown) onto the threaded portions on the outside of the rack. Preferably two such nuts are provided for such purpose for each hose shank. Of course, other means for mounting the hose shanks on the hose rack may be provided, so long as a pair of hose shanks are supported, one at each side of the rack, for each hose.

The hoses used in the invention are preferably made of an elastomeric material that is capable, under the influence of fluid pressure and in cooperation with the testing wheel assembly (to be subsequently described), of simulating the effect of a pressurized vehicle tire on the samples to be tested. In order to provide this effect, the hose assembly also includes means (not shown) for pumping a fluid such as air into each hose and for maintaining fluid pressure within the hose so as to apply a resulting pressure to the interior walls of the hose. Such means may be attached to the threaded portions 84 of the hose shanks 80 on one side of the hose rack, with the threaded portions of the hose shanks on the other side being capped off.

By comparing FIGS. 1 and 4, and 2 and 5, it can be seen that doors 40, and 50 and 52 will provide access to the hose assembly of the preferred embodiment of the invention.

The apparatus also includes a testing wheel assembly 90 (best shown in FIGS. 7, 8 and 9) that is supported by the frame 12 and disposed above hose assembly 62 within testing chamber 14. The testing wheel assembly includes a loading wheel carrier 92 which is adapted for reciprocating movement on a track comprised of a pair of upper rails 94 and a pair of lower rails 96 (shown in FIGS. 1 and 2). Rails 94 and 96 are securely attached to the frame components by welding or other convenient means, and are adapted to support rolling wheels 98, which are disposed at either end of wheel supports 100a and 100b. Wheel support 100a is located at the front of assembly 90, and wheel support 100b is located at the rear.

Loading wheel carrier 92 is comprised of a pair of side plates 102 for each loading wheel 104, one of which is provided for each hose in the hose assembly. Preferably, the testing machine is adapted for simultaneously testing a plurality of samples, using a hose and loading wheel for each sample. Thus, as shown in the drawings, apparatus 10 is adapted for simultaneously testing three samples.

Top carrier plate 106, having elongated slot 108 therein, is attached to each of side plates 102 by welding or other suitable means, as are wheel supports 100a and 100b. The testing wheel assembly also includes an elongated loading wheel arm 110 for each hose, which arm has a first end 114 and a second end 116. The first end of each loading wheel arm is pivotally attached, by means of pivot pin 118, to the loading wheel carrier, and the loading wheel for each arm is mounted on an axis 120 that is supported at the second end 116 of the arm. A loading cylinder 122 is provided for each loading wheel, which cylinder is mounted on the loading wheel carrier 92 and which is adapted for applying a downwardly-directed load to the wheel with which it is associated. Preferably, the loading cylinder of the testing wheel assembly is a pneumatic cylinder. In addition, it is also preferred that the apparatus include a load cell (not shown) for each loading cylinder, which load cell is used to calibrate and measure the load that is applied to the wheel by the loading cylinder.

Figure 7:
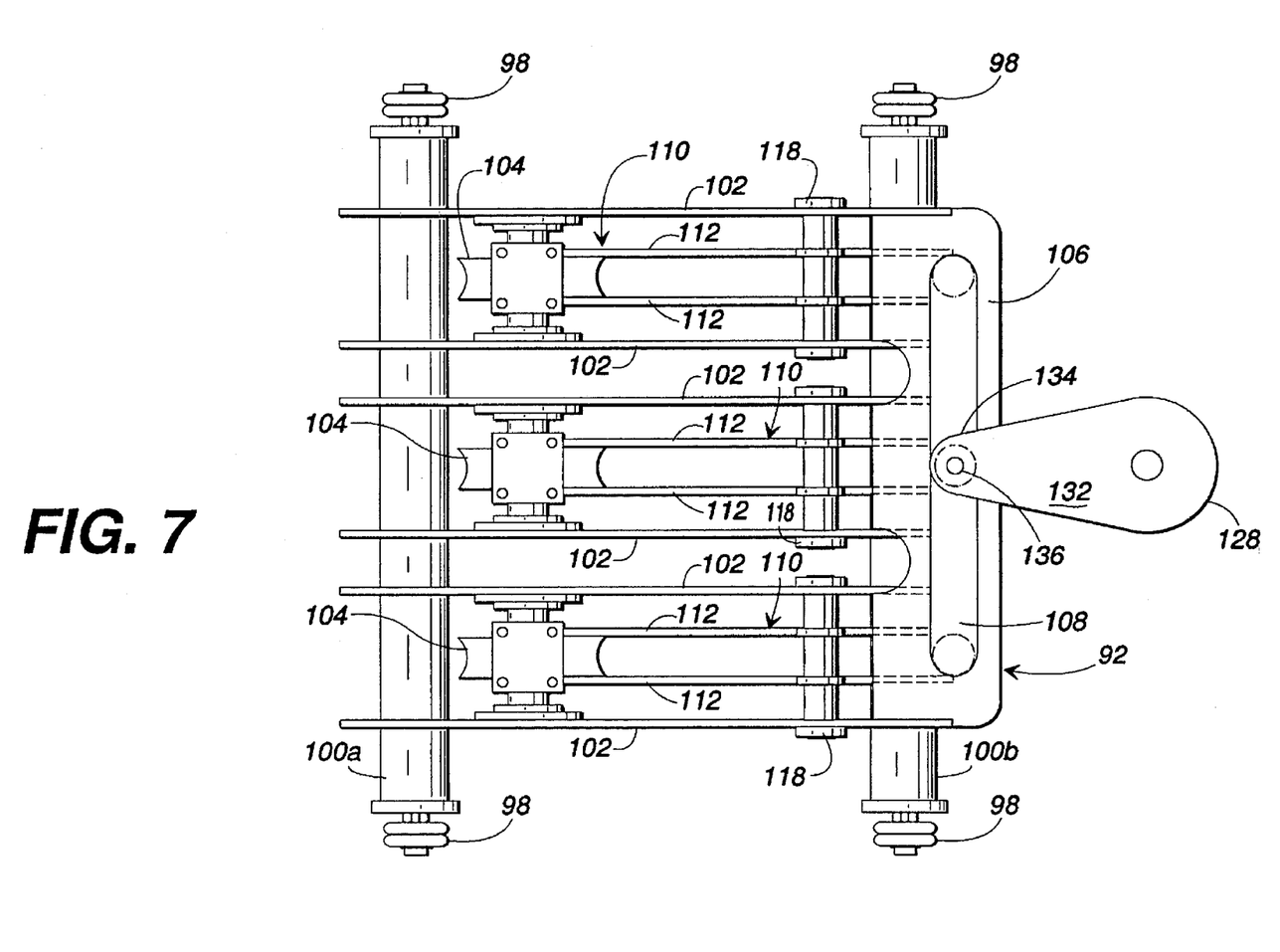
FIG. 7 is a top view of a portion of the testing wheel assembly of the apparatus of FIG. 1.
Figure 8:
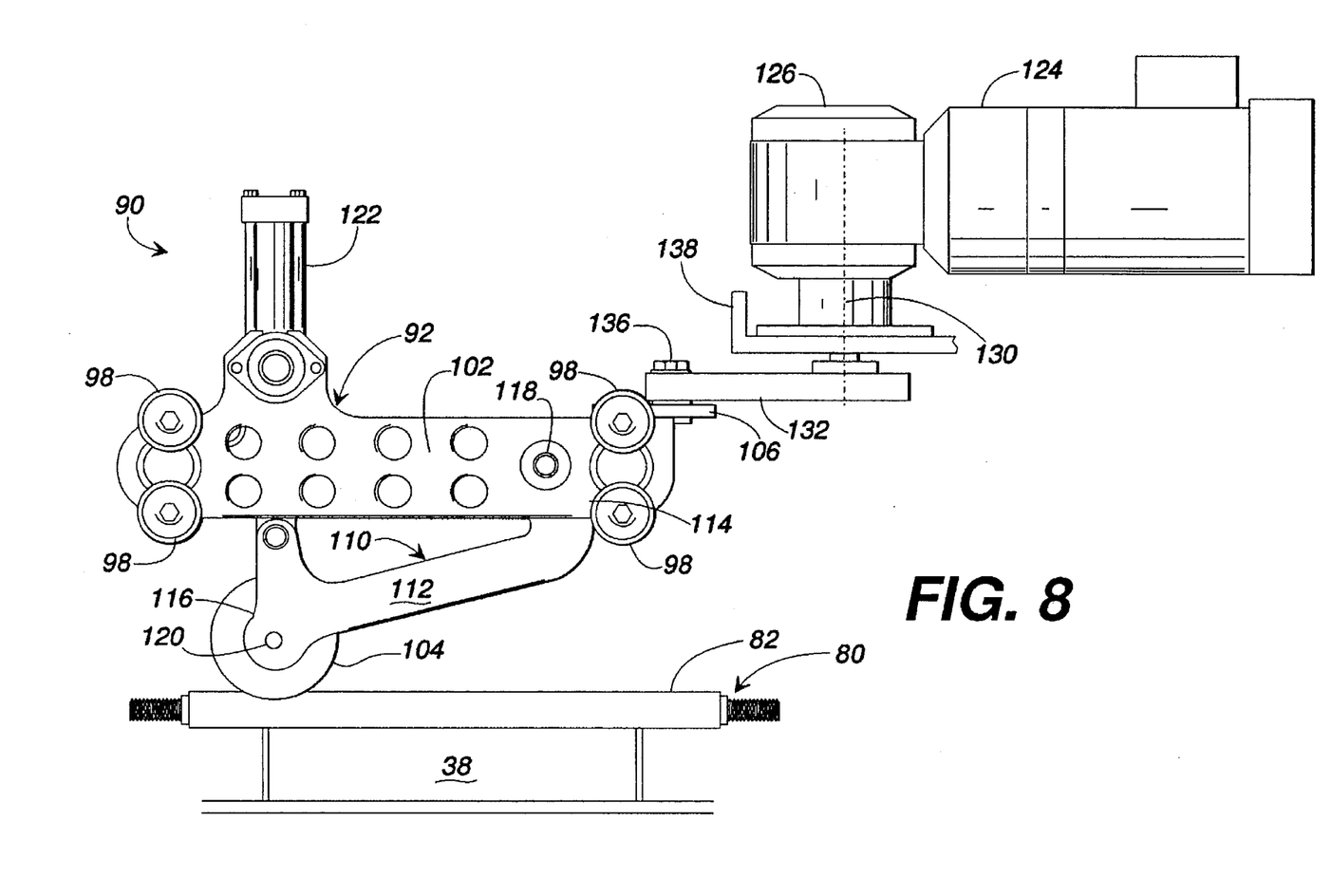
FIG. 8 is a plan view of the testing wheel assembly, a portion of the hose assembly and a test sample of the apparatus of FIG. 1, showing the wheel of the testing wheel assembly under load and in contact with a hose of the hose assembly, whereby the hose is deflected downwardly onto the sample.
Figure 9:
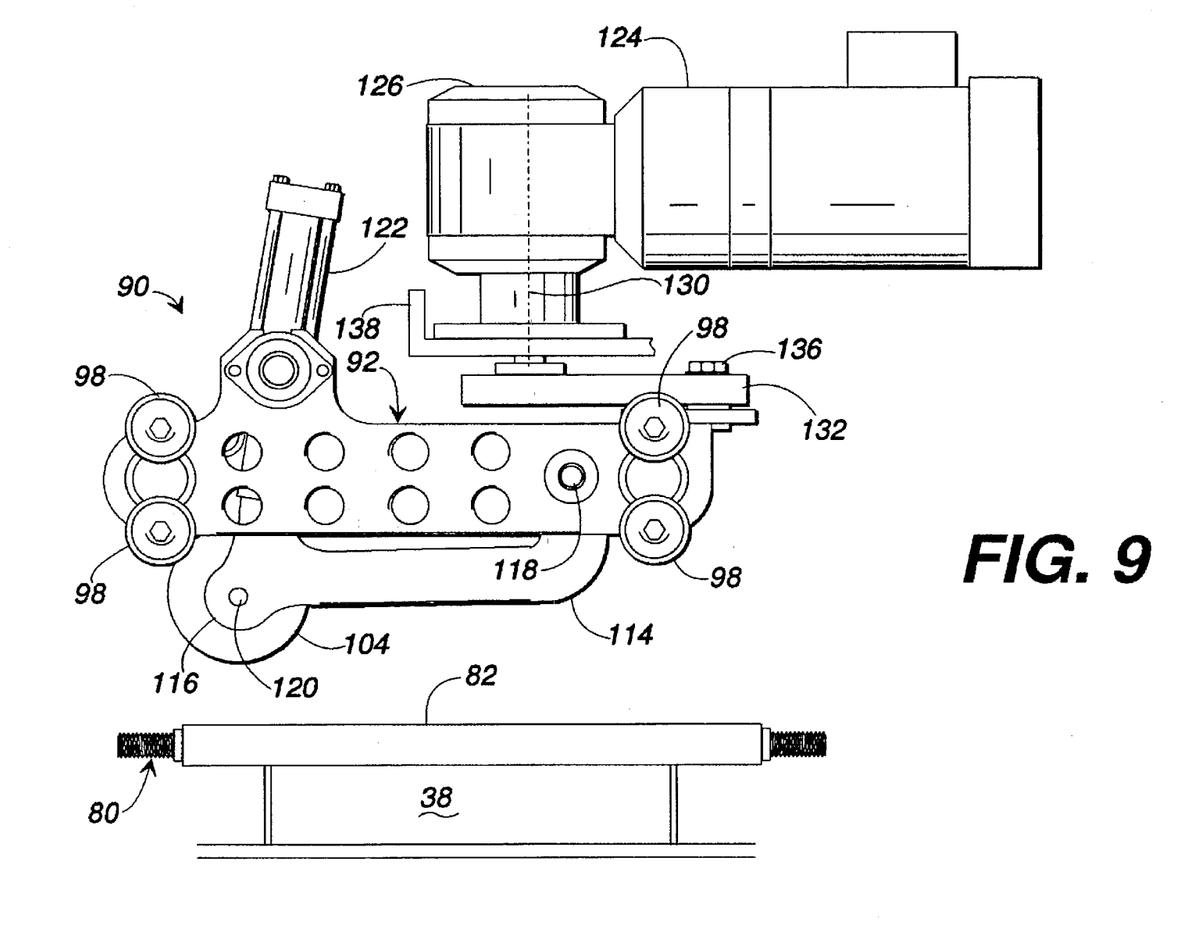
FIG. 9 is a plan view of the testing wheel assembly, a portion of the hose assembly and a test sample of the apparatus of FIG. 1, showing the loading cylinder of the testing wheel assembly retracted so that the wheel is not in contact with a hose of the hose assembly.

As shown in the drawings, especially FIGS. 2, 8 and 9, the testing wheel assembly 90 is disposed above the hose assembly 62 so that each wheel 104 is disposed above a hose 82. As shown in FIGS. 7 and 8, each wheel is preferably provided with a concave rim so as to permit it to ride atop the hose. As the loading cylinder is actuated to apply a load to the wheel (see FIGS. 2 and 8), the wheel will contact the hose and deflect the hose downwardly onto a sample. The testing wheel assembly also includes means for imparting reciprocating movement to the loading wheel carrier along the track at a controlled rate, so that each wheel will move back and forth along its associated hose.

As has previously been mentioned, loading wheel carrier 106 preferably includes slot 108 that extends across its width in a direction perpendicular to the track of the testing wheel assembly.

This slot comprises a portion of the preferred means for imparting reciprocating movement to the loading wheel carrier along the track. The preferred apparatus also includes motor 124, which is mounted outside of the testing chamber, and gear box 126, by which the rotational motion of the output shaft of the motor may be slowed to a manageable speed. Good results have been obtained when motor 124 has a one-horsepower (746 watts) power rating.

As shown in FIGS. 7 and 8, the output shaft of motor 124 is connected, through gearbox 126 to first end 128 of elongated motor arm 132, so that actuation of the motor causes the shaft (represented by centerline 130) to rotate and sweep arm 132 through a circle defined by second end 134 thereof. Bolt 136 is attached to the second end of the motor arm, in such manner as to be adapted to slidingly engage slot 108 of the loading wheel carrier. The length of slot 108 is at least twice the distance between the centerline of bolt 136 and the centerline 130 of the shaft, so that as the shaft rotates, the rotational motion of the shaft will be converted by the action of the bolt in the slot to reciprocating motion of the loading wheel carrier along the track at a controlled rate. Gearbox 126 is supported by frame member 138, as shown in FIGS. 8 and 9.

The testing wheel assembly is particularly designed to be strong, yet light in weight. Preferably, therefore, the side plates, top plate and wheel supports are made from aluminum or other suitable metal. In addition, side plates 102 may also be perforated, in a manner such as is shown in the drawings, to reduce their weight. A comparison of FIGS. 1 and 4, and 2 and 5, will reveal that doors 40, and 50 and 52 will provide access to the testing wheel assembly of the preferred embodiment of the invention.

Apparatus 10 also includes an immersion pan 140 into which sample tray 36 may be placed in the chamber without mechanical interference between the pan and the hose assembly or between the pan and the testing wheel assembly. Preferably, the apparatus also includes lifting means, such as hydraulic cylinder 142, for lifting the immersion pan from a position beneath the sample tray into a position wherein the pan will contain the sample tray so that upon filling the pan with water, the samples in the sample tray will be submerged in the water. The apparatus also includes means for filling the immersion pan with water, such as pump 144, which is attached to water supply tank 145 through incoming supply line 146, and which pumps water to fill the immersion pan through pump line 148 to outlet 150, mounted in the floor of the pan. Overflow pipe 151 permits water that overflows from the immersion pan to drain back into tank 145. Preferably, the tank and pan are constructed of stainless steel or other suitable material, and are configured so as to be supported and constrained by surrounding components of frame 12. By comparing FIGS. 1 and 4, it can be seen that door 40 will provide access to the immersion pan and associated components of the preferred embodiment of the invention. Similarly, by comparing FIGS. 2 and 5, it can be seen that door 60 will provide access to the pump and associated components.

The testing machine preferably also includes heating means for raising the temperature of the testing chamber, cooling means for reducing the temperature of the testing chamber and control means for maintaining such temperature with little variation during operation of the apparatus.

Thus, apparatus 10 includes means for controlling the temperature in the testing chamber, such as heater 152, thermostat 154, and an air conditioner comprised of condenser 156, evaporator 158, controls 159 and a fan (not shown). In addition, louver 48 is aligned with condenser 156, as may be seen by a comparison of FIGS. 1 and 4, to permit ambient air contact with the condenser. These components of the apparatus permit testing to be carried out under environmental conditions which simulate various weather conditions. Thus, for example, testing may be carried out at 105° F. (40.8° C.), to simulate the hottest summertime temperatures likely to be encountered, or at 40° F. (4.8° C.), to simulate colder wintertime conditions. The apparatus is preferably provided with the means to control the temperature in the testing chamber and to maintain it at a relatively constant level, within a range of about 1 ° F. (1.8° C.), anywhere within the range of approximately 40° F. (4.8° C.) to approximately 140° F. (60.3° C.).

Preferably, the apparatus also includes a preconditioning tray 160 within testing chamber 14, into which samples may be placed for preconditioning at the temperature of operation of the apparatus. The preconditioning tray is therefore designed to hold the samples for a period of time within the testing chamber to allow them to assume the temperature of the chamber prior to testing. By comparing FIGS. 2 and 5, it can be seen that door 58 will provide access to the preconditioning tray of the preferred embodiment of the invention.

In order to use the apparatus to test various asphalt pavement compositions or asphalt concrete compositions for surface wear, including rutting and stripping, and fatigue, samples of such compositions must be prepared. Such samples are prepared under conditions that are designed to simulate the conditions under which the mixing, application and compaction of asphalt concrete pavement is carried out. Preferably, a sample is prepared by thoroughly mixing the components of the asphalt concrete composition, and then compacting the composition in a mold that is designed to fit the sample tray. Preferably, the mold is comprised of ultra-high molecular weight (UHMW) plastic, although other materials may also be used, as is known. Good results have been obtained when samples are prepared that are approximately 4.92 inches (12.5 cm) wide by approximately 11.81 inches (30 cm) long by approximately 2.63 inches (6.7 cm) thick, although samples may be prepared of any convenient size and in any convenient shape. The samples as prepared should be cured or aged for sufficient time to insure that they will be stable at temperatures within the range of testing, preferably approximately 40° F. (4.8° C.) to approximately 140° F. (60.3° C.).

When the apparatus is used to test samples of pavement compositions, one or more test samples are placed in the sample tray, and fluid, such as air, is pumped into each hose. Fluid pressure is maintained in each hose so as to apply a resulting pressure to its interior walls.

As the load is applied, the strain gauge will measure the strain applied to the sample. Preferably, a load of 100 lbs (45.4 kg) is applied by the loading cylinder to the wheel, and a pressure of 100 psi (6900 kPa) is maintained within the hose. It is also preferred that the temperature within the testing chamber be maintained at approximately 105° F. (40.8° C.).

When the apparatus is used to test a sample for fatigue, the preferred rectangular sample may be removed from its mold and placed in a support structure on the sample tray, such as may be provided by end support members 162 and 164, so that it is supported at each end. An elastomeric pad (not shown) may then be placed beneath the unsupported central portion of the sample, and a strain gauge (not shown) placed beneath the sample between it and the pad. The loading cylinder for each loading wheel may then be actuated so as to apply a downwardly-directed load to each such wheel. The wheel will contact the hose beneath it and cause it to deflect downwardly onto the sample therebelow. The effect on the sample oft he loaded wheel on the pressurized hose will therefore serve to simulate the effect on the pavement of a loaded vehicle having pressurized tires. Reciprocating movement may then be imparted to the loading wheel carrier along the track at a controlled rate, while the loading cylinder for each loading wheel is activated so as to apply a downwardly-directed load to each such wheel, so that each wheel will move back and forth along a hose while under the influence of the load. The reciprocating movement under load may be maintained on the sample for a predetermined number of cycles, such as up to 10,000 loaded wheel passes, and readings from the strain gauge may be interpreted to indicate if fatigue cracking has occurred, and if so, the degree of its severity. Such information may be used to predict the susceptibility of the pavement composition to fatigue cracking.

When the apparatus is used to test a sample for rutting, the preferred rectangular sample is placed on the sample tray within a support structure, such as may be provided by side supports (not shown) and base plate 166, that is designed to support the sides of the sample and to provide an unyielding base beneath the sample. The support of the sides is preferred in order that the asphalt concrete in the sample not be allowed to deform laterally under load, since the asphalt concrete in a wheel path of a roadway is practically constrained from lateral deformation when subjected to wheel loads by the asphalt concrete in the roadway on either side of the path.

The loading cylinder for each loading wheel may then be actuated so as to apply a downwardly-directed load to each such wheel. The wheel will contact the hose beneath it and cause it to deflect downwardly onto the sample therebelow. The effect on the sample of the loaded wheel on the pressurized hose will therefore serve to simulate the effect on the pavement of a loaded vehicle having pressurized tires. Reciprocating movement may then be imparted to the loading wheel carrier along the track at a controlled rate, while the loading cylinder for each loading wheel is actuated so as to apply a downwardly-directed load to each such wheel, so that each wheel will move back and forth along a hose while under the influence of the load. The reciprocating movement may be maintained for a predetermined number of cycles, such as up to 10,000 loaded wheel passes, and measurements may be taken of the rutting that occurs in the sample at appropriate intervals. Measurements may also be taken more or less continuously, and a graph prepared showing rutting versus the number of loaded wheel passes. Preferably, such measurements are made by means (not shown) for measuring the distance from a reference point on the testing wheel assembly to the bottom of the loaded wheel to determine the depth of rutting. One device by which such measurements may be taken is a linear variable differential transformer, although other devices and means as are known to those skilled in the art to which this invention relates may also be used. If a linear variable differential transformer is employed, it may be provided with a probe (not shown) that is incorporated into loading cylinder 122, and a differencing/sum unit (also not shown) which measures the distance travelled by the prove as the cylinder is activated to apply a load to the loaded wheel. Such measurements may then be used to predict the rutting tendency of the pavement.

The effects of stripping are similar to the effects of rutting. Therefore, when the apparatus is used to test a sample for stripping, the preferred rectangular sample is placed on the sample tray within the support structure that is used for the rutting test. The samples are then placed in the immersion pan in the chamber. Preferably, this is accomplished by lifting immersion pan 140, using hydraulic cylinder 142, from a position beneath sample tray 36 into a position wherein the pan will contain the sample tray without mechanical interference between the pan and the hose assembly or between the pan and the testing wheel assembly. Upon filling of the pan with water, the samples in the sample tray will be submerged therein. Reciprocating movement may then be imparted to the loading wheel carrier along the track while the loading cylinder for each loading wheel is actuated so as to apply a downwardly-directed load to each such wheel, so that each wheel will move back and forth along a hose while under the influence of the load. The reciprocating movement may be maintained for a predetermined number of cycles, such as up to 10,000 loaded wheel passes, and measurements may be taken of the stripping that occurs in the sample at appropriate intervals. Measurements may also be taken more or less continuously, and a graph prepared showing stripping versus the number of loaded wheel passes. Preferably, such measurements are made by means (not shown) for measuring the distance from a reference point on the testing wheel assembly to the bottom of the loaded wheel to determine the depth of stripping, such as are employed in the rutting testing described herein before. Such measurements may then be used to predict the stripping tendency of the pavement.

Although this description contains many specifics, these should not be construed as limiting the scope of the invention but as merely providing illustrations of some of the presently preferred embodiments thereof, as well as the best mode contemplated by the inventors of carrying out their invention. The invention, as described herein, is susceptible to various modifications and adaptations, and the same are intended to be comprehended within the meaning and range of equivalents of the appended claims.

What is claimed is:

1. An apparatus for testing one or more pavement test samples, said apparatus comprising:

a) a frame which supports and encloses a testing chamber;

b) a sample tray that is supported by the frame within the chamber and is adapted for holding one or more test samples;

c) a hose assembly which is supported by the frame and disposed above the sample tray within the chamber, which assembly comprises:

1) one or more elongated, hollow, flexible hoses, wherein a hose is provided for each test sample to be tested;

2) a hose rack which is adapted for supporting a pair of hose shanks for each hose, one at each side of the rack, said hose rack being provided with a pair of hose shanks for each hose so that each hose is attached at each end to a hose shank and thereby disposed, along an axis extending generally in a straight line from one side of the rack to the opposite side, above a test sample in the sample tray in such fashion that the hose may be deflected to contact at least a substantial portion of the sample;

3) means for pumping a fluid into each hose and for maintaining fluid pressure within the hose so as to apply a resulting pressure to the interior walls of the hose;

d) a testing wheel assembly that is supported by the frame and disposed above the hose assembly within the chamber, which assembly comprises:

1) a loading wheel carrier which is adapted for reciprocating movement on a track;

2) an elongated loading wheel arm for each hose, which arm has a first end and a second end, wherein said first end is pivotally attached to the loading wheel carrier;

3) a loading wheel for each arm, which wheel is mounted on an axis that is supported at the second end of the arm, whereby each wheel is disposed above a hose;

4) a loading cylinder for each loading wheel, which cylinder is mounted on the loading wheel carrier and adapted for applying a downwardly-directed load to such wheel, whereby such wheel will contact a hose and deflect the hose downwardly onto a sample;

5) means for imparting reciprocating movement to the loading wheel carrier along the track at a controlled rate, so that each wheel will move back and forth along a hose;

e) an immersion pan in the chamber which is adapted for receiving the sample tray without mechanical interference between the pan and the hose assembly or between the pan and the testing wheel assembly;

f) means for filling the immersion pan with water; and g) means for controlling the temperature in the testing chamber;

h) said apparatus being adapted to permit testing for fatigue or for rutting of a sample:

when one or more test samples are placed in the sample tray; and fluid is pumped into each hose and fluid pressure maintained therein so as to apply a resulting pressure to the interior walls of each hose; and the loading cylinder for each loading wheel is actuated so as to apply a downwardly-directed load to each such wheel; and reciprocating movement is imparted to the loading wheel carrier along the track at a controlled rate, while the loading cylinder for each loading wheel is actuated so as to apply a downwardly-directed load to each such wheel, whereby each wheel will contact a hose under the influence of the load and deflect such hose downwardly onto a sample, so that each wheel will move back and forth along a hose while under the influence of the load; and i) said apparatus being adapted to permit testing for stripping of a sample:

when one or more samples are placed into the immersion pan in the chamber, and the pan filled with water, and reciprocating movement imparted to the loading wheel carrier along the track while the loading cylinder for each loading wheel is actuated so as to apply a downwardly-directed load to each such wheel, whereby each wheel will contact a hose under the influence of the load and deflect such hose downwardly onto a sample, so that each wheel will move back and forth along a hose while under the influence of the load.

2. The apparatus of claim 1, which includes means for lifting the immersion pan from a position beneath the sample tray into a position wherein the pan will contain the sample tray so that upon filling the pan with water, the samples in the sample tray will be submerged in the water.

3. The apparatus of claim 1, wherein the sample tray is mounted on a track in sliding engagement therewith, said tray being adapted for sliding movement from a first position beneath the hose assembly and the testing wheel assembly to a second position that provides more convenient access to the samples in the tray.

4. The apparatus of claim 1, wherein the loading wheel carrier includes a slot that extends across its width in a direction perpendicular to the track of the testing wheel assembly, and wherein the means for imparting reciprocating movement to the loading wheel carrier along the track comprises:

a) a motor;

b) an elongated motor arm having a first end and a second end, wherein the first end is attached to a shaft of the motor or a shaft turned by the motor so that actuation of the motor causes the shaft to rotate and sweep the arm through a circle defined by the second end thereof; and c) a bolt that is attached to the second end of the motor arm, said bolt being adapted to slidingly engage the slot of the loading wheel carrier;

d) wherein the length of slot is at least twice the distance between the bolt and the shaft, so that as the shaft rotates, the rotational motion of the shaft will be converted by the action of the bolt in the slot to reciprocating motion of the loading wheel carrier along the track.

5. The apparatus of claim 1, wherein the loading cylinder of the testing wheel assembly is a pneumatic cylinder.

6. The apparatus of claim 1, which includes a load cell for each loading cylinder, which load cell is used to calibrate and measure the load that is applied to the wheel by the loading cylinder.

7. The apparatus of claim 1, which includes means for measuring the distance from a reference point on the testing wheel assembly to the bottom of the loaded wheel to determine the depth of rutting.

8. The apparatus of claim 1, which is adapted for simultaneously testing a plurality of samples, using a hose and loading wheel for each sample.

9. The apparatus of claim 1, which includes heating means for raising the temperature of the testing chamber, cooling means for reducing the temperature of the testing chamber and control means for maintaining such temperature with little variation during operation of the apparatus.

10. The apparatus of claim 9, which includes a preconditioning tray within the testing chamber, said preconditioning tray being adapted for receiving samples for preconditioning at the temperature of operation of the apparatus prior to testing.

* * * * *